United States Patent
Payne

(10) Patent No.: US 6,532,836 B1
(45) Date of Patent: Mar. 18, 2003

(54) GRAIN BIN PROBE PORT AND SAMPLING METHOD

(76) Inventor: Lynn Payne, 1003 31st Ave., Camanche, IA (US) 52730

( * ) Notice: Subject to any disclaimer, the term of this patent is extended or adjusted under 35 U.S.C. 154(b) by 0 days.

(21) Appl. No.: 09/681,809

(22) Filed: Jun. 8, 2001

(51) Int. Cl.[7] .............................. G01N 1/16; G01N 1/26; G01N 1/00
(52) U.S. Cl. ................ 73/863.31; 73/863.85; 73/863
(58) Field of Search ................ 73/323, 863.81, 73/863.85, 863; 29/428; 292/59; 70/164; 307/116

(56) References Cited

U.S. PATENT DOCUMENTS

| | | | |
|---|---|---|---|
| 840,943 A | | 1/1907 | Ingold |
| 1,966,712 A | | 7/1934 | Fisher et al. |
| 3,065,637 A | | 11/1962 | Landes |
| 3,950,653 A | * | 4/1976 | Kirkpatrick ............... 307/116 |
| 3,950,971 A | * | 4/1976 | Karls ........................ 70/164 |
| 3,991,913 A | * | 11/1976 | Steffen ....................... 222/156 |
| 4,133,457 A | * | 1/1979 | Klassen ...................... 222/212 |
| 4,625,570 A | * | 12/1986 | Witherspoon et al. ... 73/863.81 |
| 4,663,978 A | | 5/1987 | Lenski et al. |
| 4,688,835 A | * | 8/1987 | Wu ............................. 292/59 |
| 4,838,094 A | * | 6/1989 | Baldock .................. 73/863.81 |
| 5,481,790 A | * | 1/1996 | Koreis et al. ................ 29/428 |
| 5,604,996 A | | 2/1997 | Bestwick et al. |
| 5,735,168 A | * | 4/1998 | Harrison ..................... 73/323 |
| 6,141,886 A | * | 11/2000 | Watson et al. ............... 34/166 |

OTHER PUBLICATIONS

GSI Grain Systems, Farm Storage Bins/Silos, pp. 5–7, Sep. 1998.

* cited by examiner

Primary Examiner—Daniel S. Larkin
Assistant Examiner—Rodney Frank
(74) Attorney, Agent, or Firm—Glenn Johnson

(57) ABSTRACT

A port structure is disclosed that may be placed at differing height intervals in the side of the on-farm or smaller grain storage bin. The port is sealed with the sealing apparatus to prevent the introduction of unwanted moisture or insects into the storage cavity of the grain bin. A standard sharp pointed probe available in the industry is utilized with the invention. Once the sealed cap is removed, the probe is inserted through the port horizontally into the stored grain to obtain grain samples at whatever intervals are provided by the standard probe mechanism. Also disclosed is a method for sampling from a horizontal cross section of a particulate matter storage bin.

11 Claims, 5 Drawing Sheets

GRAIN BIN PROBE PORT AND SAMPLING METHOD

BACKGROUND OF INVENTION

Millions of bushels of grain are stored in various facilities throughout the United States. A significant portion of this grain is stored in smaller on-farm grain bin storage facilities. These on-farm storage facilities are primarily made of rolled corrugated, galvanized steel. There has historically been a need to test the grain within these facilities from time to time for moisture content, the presence of mold and rot, and for insect problems. Of more recent concern is the need to obtain representative samples from on-farm storage facilities so as to test to ensure the absence of genetically modified crops commingled with other crops stored within the bin.

Historically, grain samples for testing have been obtained during the loading process when grain was being augered or otherwise moved through a chute to be dumped into the storage facility, usually through a top located hatch assembly. Other known methods of sampling grain called for the use of pointed probes, boring apparatus or other devices which were inserted into the stored grain through the top of the storage facility or, otherwise, called for an individual to enter the storage facility standing on the grain so as to obtain a vertically drawn sample. These methods were both inconvenient, did not obtain grain samples representative of the bin contents, and, in the case of the method requiring entry of an individual into the storage bin, were potentially dangerous.

Various patents have been issued relating to grain sampling methods, devices and probes. U.S. Pat. No. 840,943 teaches the use of an internal chamber permanently affixed within the grain storage bin. Grain samples are obtained by use of slide valves which open and close inlet ports. The grain sampling apparatus extends vertically within the storage facility and, depending upon which port is open, a sample can be obtained from different levels of the grain stored within the grain bin.

U.S. Pat. No. 1,966,712 features the use of a mechanical apparatus which obtains samples of grain as grain passes through chutes while being transported into or out of the grain storage bin.

U.S. Pat. No. 3,065,637 teaches a grain sampling methodology again retrieving the grain sample vertically through the top of the grain storage facility. The probe consists of an auger-like device which will penetrate the stored grain from the top down. The device is inserted through the stored corn down to the desired level, and samples are obtained. The device is designed to be used by a single individual standing on top of the stored grain within the grain storage facility.

U.S. Pat. No. 4,625,570 teaches the use of a telescopic sampling apparatus attached to the outer wall of a vertical pipeline or chute through which grain is being transported. The primary use of this device is to obtain grain samples which are being moved for storage into a grain storage bin or moved from one storage locale to a differing locale. The device utilizes a hollow tube inserted within another hollow tube. The tube assembly can be telescopically inserted through a track assembly affixed to the outer wall of a chute or tube, thereafter being rotated to expose the cradle into which grain will flow as it passes by gravity feed through the chute or tubing in which the sampling device is installed. Thereafter, the outer tube is again rotated to close the cradle with the grain sample captured therein, and the device is manually telescopically withdrawn from the chute. Once withdrawn, the inner hollow tube is rotated until its opening matches the opening on the bottom side of the exterior tube thereby allowing the grain sample to drop freely into a collection plate which is used to carry the grain to the laboratory for testing. The apparatus taught by the '570 patent is a permanent telescopic device which is mounted to the exterior wall of the chute or vertical pipe. The device is not designed, nor does the patent teach the use of this type of a device in a grain storage bin wherein grain has already been accumulated and stored.

U.S. Pat. No. 4,838,094 teaches the use of an internal apparatus located within a grain storage bin. This apparatus allows for the ability to retrieve grain samples of grain being loaded within the top port of the bin or, further, to retrieve grain samples from grain already placed and housed within the bin, thereafter transporting the grain to an exterior tubular chamber from which the grain sample can be retrieved for testing purposes.

U.S. Pat. No. 5,604,996 teaches the use of a mechanical apparatus which facilitates both the drying of the grain being placed in storage as well as retrieval of samples of grain for testing purposes, which grain is entering the bin by being dropped through the top port of the grain storage facility. The samples so retrieved are transported through tubing to a flow splitter which divides the flow of grain coming through the tube so only a small fraction thereof is diverted to the outer collection tube for purposes of testing.

The present invention differs from the prior art existent in the field and evident in the above referenced United States patents in two significant ways. First, it is not a cumbersome apparatus which is housed within the grain storage facility thereby diminishing the capacity of the facility and creating the opportunity for malfunction. Secondly, the current invention allows for the horizontal approach to obtain grain samples which allows for a more thorough sampling and testing of the grain contents while using a minimum of sampling points.

The present invention consists of a port which may be placed at differing height intervals in the side of the on-farm or smaller grain storage bin. The port is sealed with the sealing apparatus to prevent the introduction of unwanted moisture or insects into the storage cavity of the grain bin. A standard sharp pointed probe available in the industry is utilized with the invention. Once the sealed cap is removed, the probe is inserted through the port horizontally into the stored grain to obtain grain samples at whatever intervals are provided by the standard probe mechanism.

The standard wagon load of grain consists of 220 bushels. Grain is typically augered up to the top of the grain storage bin and enters by gravity feed through the top hatch. As each wagon load fills the bin, the grain achieves an angle of repose. This angle of repose has been measured to be about 17.5°. As shown by FIG. 5, by use of a horizontal grain probe, which use is allowed by the current invention, and because of the angle of the repose of the grain sitting in storage, different wagonloads will be obtained with the horizontal sampling mechanism. This allows for obtaining a significant number of samples which is more representative of the mix of the grain stored within the facility with a minimum of effort.

SUMMARY OF INVENTION

The grain bin probe port includes a port framing member or other port pipe attaching means such as a panel plate through which is passed a tube. The tubing is held in place within the plate either by weld assembly or by circumferential ridges creating a swedge which prevents the plate from slipping toward one end of the pipe or the other. The interior aspect of the port is covered with a shield means, for example, a shield made of elastic material. The shield is star-cut to allow for the passage of the sample probe through it to the interior cavity of the grain storage bin and, when withdrawn the shield elastically closes to prevent grain from flowing into the port pipe. The panel plate has a gasket on its back side which will seal against the exterior of the grain bin wall when installed. The seal cap assembly has a push plate affixed to the interior aspect of the seal cap shaft. The push plate will push any loose grain out of the port, through the shield, back into the storage cavity of the grain storage bin. Affixed to the seal cap shaft near its front is the seal plate against which is positioned the gasket seal. Inserted over the shaft and against the gasket seal is the cap which is threadably retained in place by use of a wing nut. Once the seal cap assembly is inserted into the port pipe with the cap coming to rest against the gasket, the wing nut is tightened expanding the gasket to hold the seal cap assembly in place and to create a water and airtight seal of the port.

DETAILED DESCRIPTION

Figure 1:
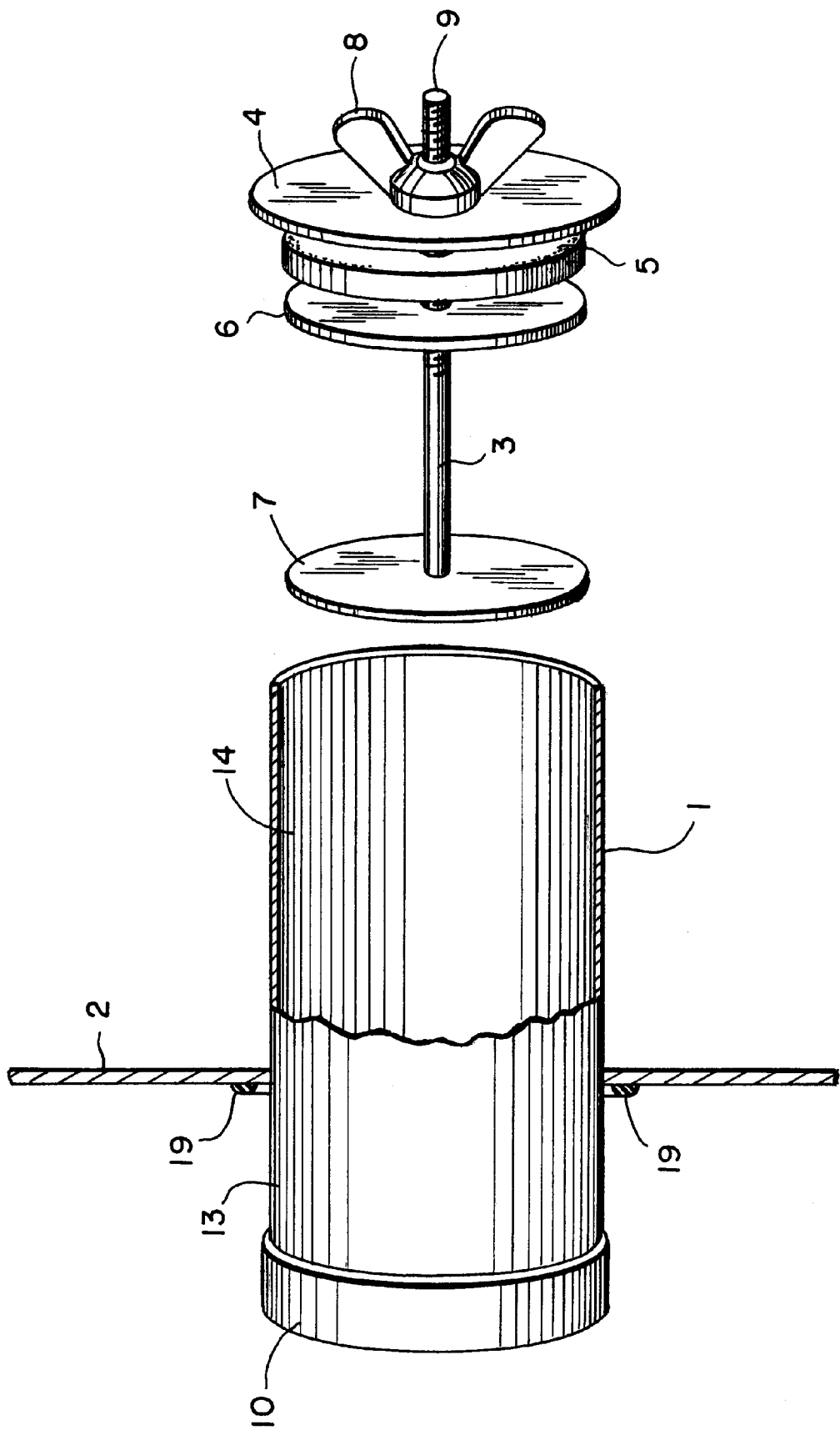
FIG. 1 is an exploded perspective of the grain bin probe port.
Figure 2:
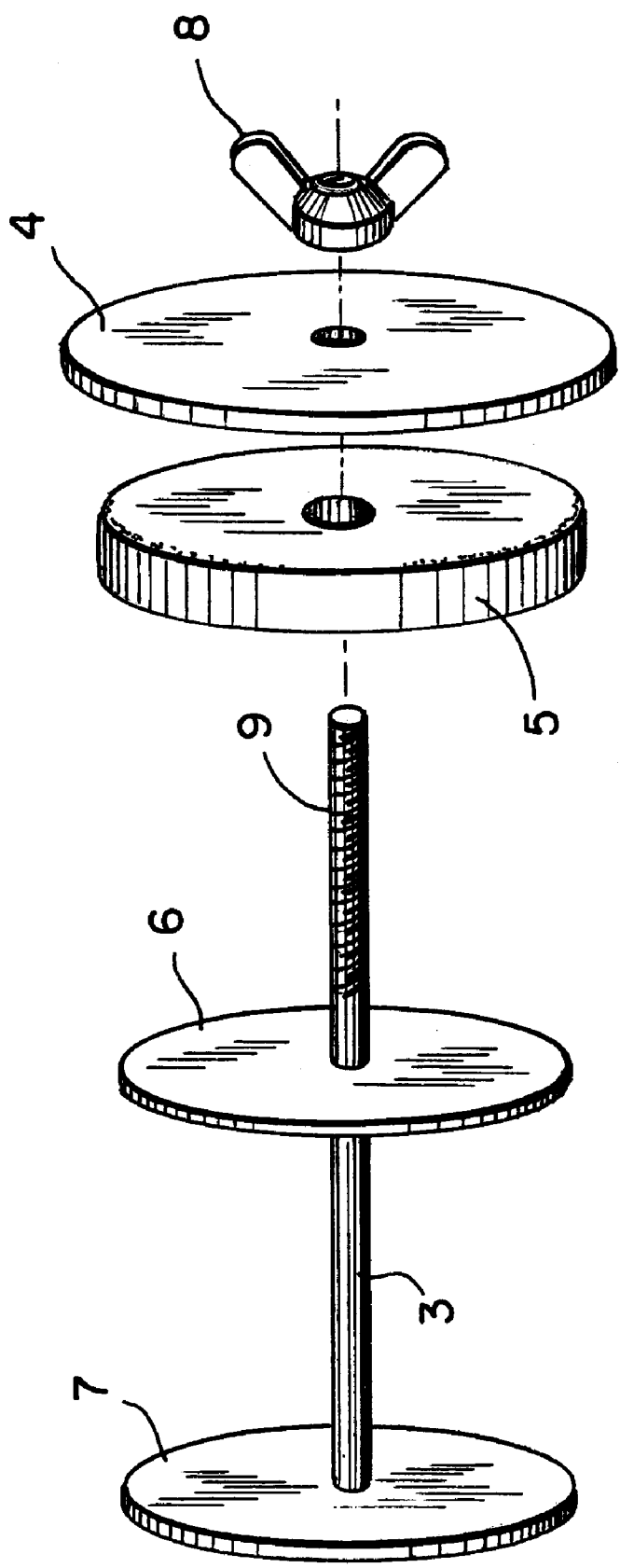
FIG. 2 is an exploded perspective view of the seal cap assembly.
Figure 3:
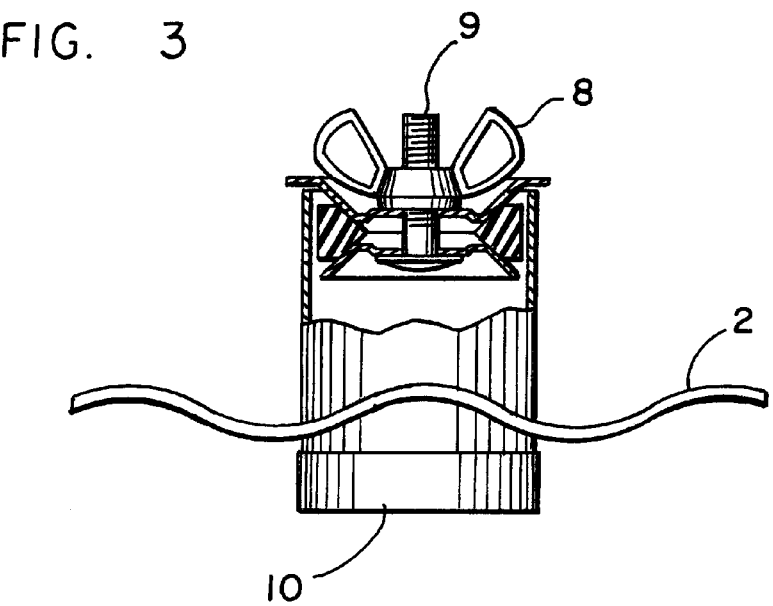
FIG. 3 is a transparent top view of a corrugated plate, port and seal cap assembly.
Figure 4:
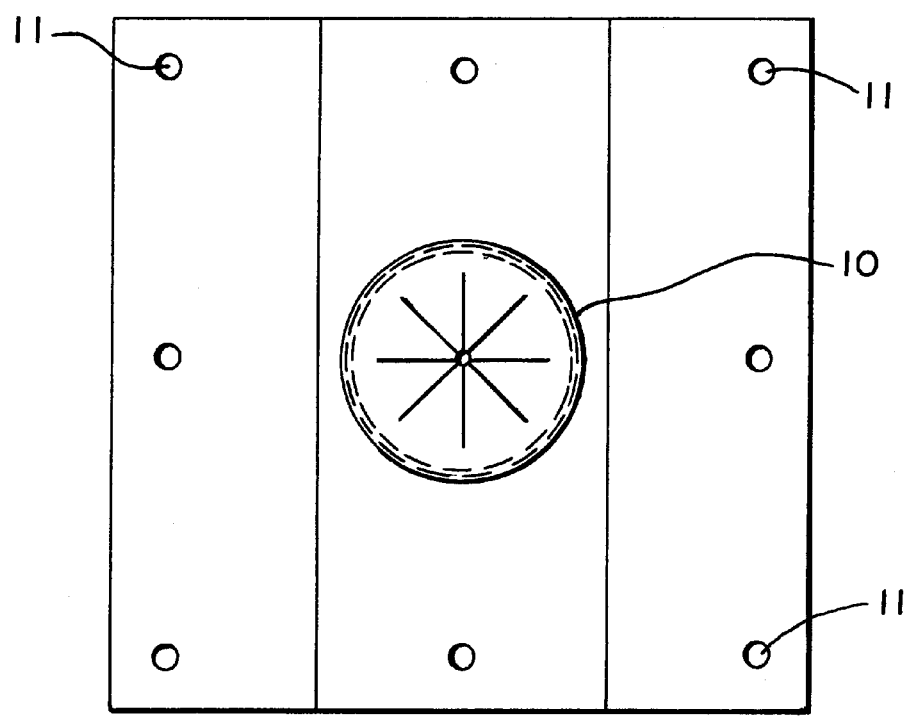
FIG. 4 is an end view of the rear shield showing the star slits contained therein.
Figure 5:
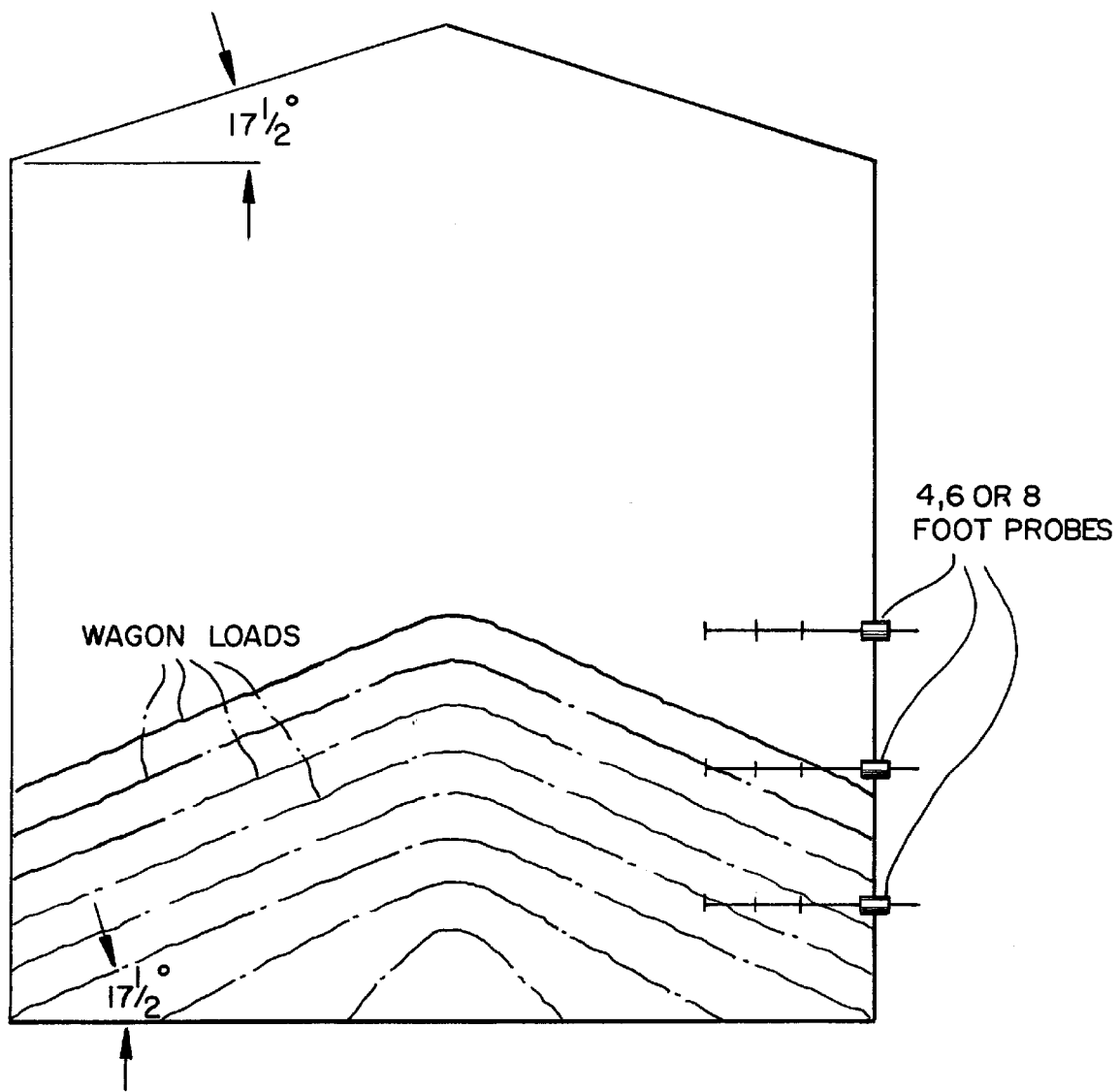
FIG. 5 shows a typical on-farm grain storage bin into which wagonloads of grain have been placed along with placement of various of the ports from which grain samples may be obtained.

The grain or other particulate storage bin probe port consists of a port pipe 1 which is inserted through the hole in a panel plate 2. Most grain storage bins upon which this invention will be used are circular in nature and made of corrugated galvanized steel. Accordingly, the panel plate 2 usually will be made of corrugated galvanized steel thus being adapted as illustrated in FIG. 3 so as to match the geometric configuration of the grain bin exterior wall.

The port pipe 1 may be welded to the panel plate 2. This is not the preferred embodiment, however, because with the use of galvanized steel there will be a need to regalvanize the panel plate 2. Instead, the preferred embodiment uses a port pipe 1 with an outer diameter slightly smaller than the diameter of the hole cut through the panel plate 2 into which it is inserted. After insertion, a tube expander is used within the port pipe 1 to bulge out the inner diameter of the port pipe 1 circumferentially on each side of the panel plate 2, thereby creating a swedge 12. This swedge 12 is a groove or slot which firmly holds the pipe in place within the panel plate 2.

The panel plate 2 has a series of guide holes 11 pre-drilled in it to allow for ease of installation. For installation, a circular hole is cut in the side of the grain storage bin to allow for insertion of the interior port pipe segment 13 into the storage cavity of the grain bin. Self-tapping screws are passed through the guide holes 11 in the panel plate 2 and into the exterior wall of the grain storage bin to firmly hold the port in place. The rear surface of the panel plate 2 has a rubberized gasket 19 affixed to it thereby creating a complete seal against the exterior wall of the grain storage bin once firmly screwed into place. It may be preferred to provide a second plate for placement on the interior of the grain storage bin sidewall opposite the first plate. Through use of an interior plate, additional structural support may be provided to the sidewall as the screws or other fasteners or attachment means such as nuts and bolts pull the plates together against the sidewall and about the port pipe.

It has been found that the outward pressure from the grain against the bin wall can be relatively small. Of course, depending on the characteristic angle of repose of the particulate material that is stored, this outward pressure may vary dramatically. However, for use with a grain such as corn, it has been found that in using the port assembly having a single panel plate, once the probe port has been pushed into a hole formed in the bin sidewall, the use of six self-tapping screws should have a maximum force of about 41.87 pounds to withstand. If stress is concentrated with approximately 20% of the stress on the four corner screws and about 80% of the stress on the center screws, then the maximum stress on any given screws may be less than 17 pounds. This is well under the 135 pounds per screw as allowed under the UL standard for #12 self tapping screws in 16 gauge material. Of course, the invention is not limited to a particular selection of fastener means, material gauge, or fastener arrangement.

In its best mode, the end of the interior port pipe segment is covered with a grain shield 10. This is a flexible cap made of an elastic plastic or rubberized material which is cut in a star configuration. This allows the sample probe to pass through the interior port opening into the grain so as to retrieve samples and, when the probe is removed, recloses to prevent or minimize grain from spilling into or through the port.

Figure 6:
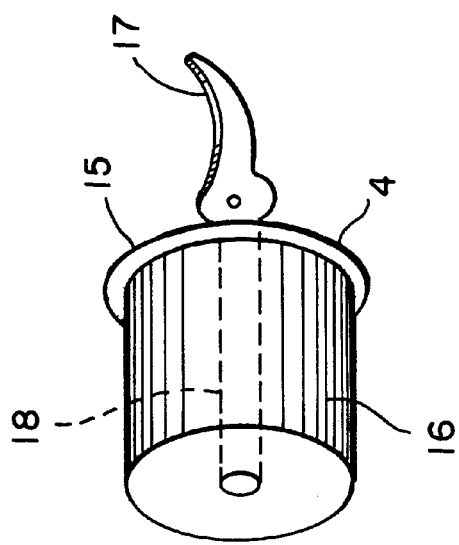
FIG. 6 shows a lever cap assembly which may be used in place of the seal cap assembly to close and seal the port.
Figure 7:
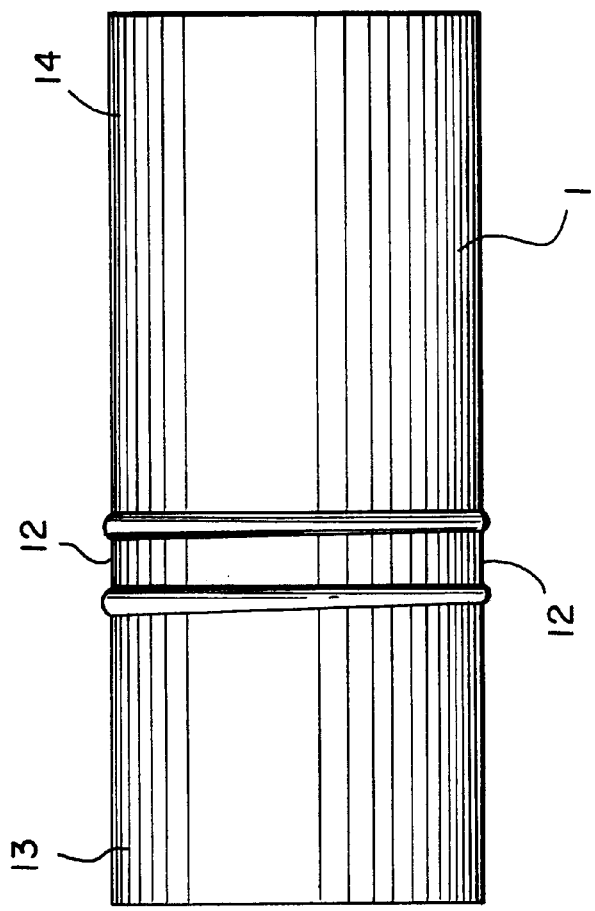
FIG. 7 shows a perspective view of the port pipe containing a swedge.

A port pipe sealing means such as a seal cap closes and seals the front exterior portion of the port. Such means may include, for example, a cap could be screwed into place with a internal gasket thereby sealing the port. Also, a frictional cap could be used with a gasket to accomplish the closure and seal of the exterior port opening. As shown in FIG. 6 a lever seal cap assembly 15 consisting of an expandable gasket 16 behind a cap 4 could be utilized. This embodiment utilizes a gasket actuating means such as cam 18 passing through and attached to the end of the expandable gasket 16. As the cap lever 17 is moved to the closed position, the cam 18 is retracted toward the cap 4 which expands the expandable gasket 16 against the inner diameter wall of the exterior port pipe segment 14 to create a seal and hold the lever seal cap assembly in place.

The preferred embodiment for the seal cap, however, consists of an at least partially threaded shaft 9 having at its rear end a circular push plate 7 and its forward end a cap 4 larger in diameter than the diameter of the exterior port pipe 14 into which it is inserted. Behind the cap 4, preferably immediately behind the cap 4, is a flexible seal gasket 5. Behind the seal gasket 5, preferably immediately behind the seal gasket 5, is a gasket plate 6 which is affixed to the shaft 9. The cap 4 is threadably retained on the shaft 9 and will float on the shaft 9 as the wing nut 8 is tightened or loosened. In use, the seal cap assembly 3 is placed within the exterior port pipe segment 14 with the push plate 7 pushing whatever may have found its way in the port back into the grain bin storage cavity. Once fully inserted, the wing nut 8 or other gasket actuating or compressing means is threadably tightened, or otherwise actuated, which pinches the gasket seal 5 between the cap 4 and the gasket plate 6 thereby expanding the gasket seal 5 radially until a firm seal is created within the port. This operates to hold the seal cap assembly 3 firmly in place and to prevent the introduction of moisture, insects or other unwanted elements into the interior of the grain storage bin.

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included within the scope of the following claims.

What is claimed is:

1. A particulate storage bin probe port for breaching a particulate material bin sidewall and allowing the selective removal of stored particulate material therefrom wherein:
   a particulate bin sidewall-traversing port pipe comprises an elongated tubular member having a generally continuous opening formed therein and having an openable shield disposed at said port pipe inner segment.

2. A method for obtaining a sample of stored particulate material from a particulate material storage bin having a sidewall, said method comprising:
   causing a tubular member having an opening formed therein to breach the sidewall, said tubular member having an openable shield disposed at said tubular member inner segment which shield comprises a generally elastic member having slits formed therein;
   sealing the breached sidewall about said tubular member;
   providing a selectively removable plug within said tubular member, said plug having a particulate material clearing end and a gasket forming end with a member extending therebetween;
   selectively removing said plug from said tubular member;
   inserting through said tubular member a removable particulate material retrieval member having openings formed therein at selected distances along said member;
   removing said particulate material retrieval member;
   replacing said plug.

3. The method of claim 2 wherein:
   the gasket forming end of the plug is an expandable and relaxable gasket and wherein the step of removing the plug comprises relaxing said gasket and wherein the step of replacing said plug comprises expanding said gasket.

4. A method for testing a selected quantity of bin-stored grain from a plurality of grain loads for the presence of genetically modified material comprising:
   determining an angle of repose characteristic of the grain to be tested;
   determining based upon said angle of repose a length of horizontal cross section necessary to be sampled in order to obtain grain from a selected number of loads;
   horizontally inserting through a sidewall of the bin an elongated sampling device of the determined length;
   removing from said bin said sampling device having a retrieved sample contained therein;
   subjecting said retrieved sample to a selected test for determining the presence of genetically modified material.

5. The method of claim 4 wherein:
   the grain is corn.

6. The method of claim 4 wherein:
   the step of subjecting said retrieved sample to a selected test for determining the presence of genetically modified material comprises:
      transferring said sample to a third party for determination and performance of an appropriate test; and
      obtaining from said third party a report of results regarding said test.

7. A grain bin probe port adapted to accommodate the retrieval of a sample of grain from a generally horizontal section of a grain bin thereby obtaining grain from a plurality of loads that have come to rest within the bin as determined by the grain's characteristic angle of repose, said grain bin probe port comprising:
   a grain bin sidewall plate, said plate having an outer face and an inner face;
   a gasket combined with said grain bin sidewall plate inner face;
   a port pipe combined with and extending through said sidewall plate, said port pipe having an exterior segment and an interior segment;
   a selectively openable grain shield disposed generally at said port pipe inner segment;
   a seal cap assembly adapted for insertion and removal from said port pipe, said seal cap assembly comprising:
      a push plate;
      a shaft fixedly combined with said push plate and extending generally outwardly therefrom, said shaft having a shaft outward end and a shaft inner end, and said shaft having a threaded portion thereon disposed generally near said shaft outer end;
      a gasket plate combined with said shaft outwardly from said push plate, said gasket plate having a gasket plate opening formed therein through which said shaft extends;
      a gasket combined with said shaft outwardly from said gasket plate, said gasket having a gasket opening formed herein through which said shaft extends;
      a cap combined with said shaft outwardly from said gasket, said cap having a cap opening formed therein through which said shaft extends;
      a compression actuator combined with said shaft outwardly from said cap.

8. The grain bin probe port of claim 7 wherein:
   said probe port engages said sidewall plate through a swedge means.

9. The grain bin probe port of claim 7 wherein:
   said probe port engages said sidewall plate through a weld means.

10. The grain bin probe port of claim 7 wherein:
    said probe port engages said sidewall plate through a fastener means.

11. A particulate storage bin probe port for breaching a particulate material bin sidewall and allowing the selective removal of stored particulate material therefrom comprising:
    a particulate bin side wall—traversing port pipe having an inner segment and an outer segment comprised of an elongated tubular members having a generally continuous opening formed therein;
    a means for securely attaching said port pipe within said particulate bin side wall;
    a port pipe sealing means for selectively sealing said port pipe;
    an openable shield comprised of a generally elastic member having slits formed therein, disposed at said port pipe inner segment.

* * * * *